(12) United States Patent
Landman et al.

(10) Patent No.: US 8,480,621 B2
(45) Date of Patent: Jul. 9, 2013

(54) DEVICE AND METHOD FOR INJECTING FLUIDS OR GELS

(76) Inventors: Mania Landman, Petah Tikva (IL); Lea Brodsky, Petah Tikva (IL); Isaac Zukier, Rosh-Ha-Ayin (IL)

( * ) Notice: Subject to any disclaimer, the term of this patent is extended or adjusted under 35 U.S.C. 154(b) by 117 days.

(21) Appl. No.: 13/050,976

(22) Filed: Mar. 18, 2011

(65) Prior Publication Data

US 2011/0230833 A1 Sep. 22, 2011

Related U.S. Application Data

(60) Provisional application No. 61/315,964, filed on Mar. 21, 2010.

(51) Int. Cl.
*A61M 5/00* (2006.01)

(52) U.S. Cl.
USPC ............................................. 604/117; 604/116

(58) Field of Classification Search
USPC ..................... 604/44, 65, 116, 117, 192, 228
See application file for complete search history.

(56) References Cited

U.S. PATENT DOCUMENTS

| | | | |
|---|---|---|---|
| 2,660,169 A | 11/1953 | Henry Malm | |
| 3,727,614 A * | 4/1973 | Kniazuk | 604/115 |
| 4,067,334 A | 1/1978 | Haller | |
| 4,108,177 A * | 8/1978 | Pistor | 604/155 |
| 4,512,767 A * | 4/1985 | Denance | 604/137 |
| 4,600,403 A | 7/1986 | Wagner | |
| 4,790,823 A * | 12/1988 | Charton et al. | 604/136 |
| 4,833,384 A | 5/1989 | Munro et al. | |
| 5,015,235 A | 5/1991 | Crossman | |
| 5,690,618 A | 11/1997 | Smith et al. | |
| RE35,986 E | 12/1998 | Ritson et al. | |
| 5,906,592 A | 5/1999 | Kriesel et al. | |
| 5,921,962 A | 7/1999 | Kriesel et al. | |
| 6,994,691 B2 * | 2/2006 | Ejlersen | 604/117 |
| 2005/0187519 A1 * | 8/2005 | Harris et al. | 604/117 |
| 2008/0015503 A1 * | 1/2008 | Jansen et al. | 604/117 |
| 2008/0027385 A1 * | 1/2008 | Freeman et al. | 604/117 |
| 2009/0062744 A1 * | 3/2009 | Weilbacher et al. | 604/192 |
| 2009/0062767 A1 * | 3/2009 | Van Antwerp et al. | 604/504 |

* cited by examiner

*Primary Examiner* — Theodore Stigell
*Assistant Examiner* — Gerald Landry, II (57) ABSTRACT

A device for successively injecting material at predetermined distances between successive injections to body tissue along a desired path of skin surface includes an injector sub-assembly having a needle configured for injecting the material into body tissue, and a displacement sub-assembly configured to facilitate precise displacement of the needle or of the device along the path between successive injections.

33 Claims, 11 Drawing Sheets

| MOTOR 8 (FOR CONTROL OF CARRIAGE 14 OF INJECTOR SUB-ASSEMBLY 300) | MOTOR 20 (FOR CONTROL OF PISTON SHIFTER) |
|---|---|
| Programming the motion profile of the motor: nominal current, holding current, microstep size, acceleration and velocity. | Programming the motion profile of the motor: nominal current, holding current, microstep size, acceleration and velocity. |
| ↓ | ↓ |
| The motor turns counter-clockwise and retracts the injector sub-assembly 300 to its fully retracted "home" position. Input 3 changes from "1" to "0". | The motor turns counter-clockwise and retracts the piston shifter to its fully retracted "home" position. Input 3 changes from "1" to "0". |
| ↓ | ↓ |
| The motor turns clockwise and extracts the injector sub-assembly 300 until the skin contact sensor detects contact with the skin, I/O2 (Input 2) changes from "0" to "1". | The motor turns clockwise and extracts the piston shifter until it contacts the piston, I/O2 (Input 2) changes from "0" to "1". |

DEVICE AND METHOD FOR INJECTING FLUIDS OR GELS

RELATED APPLICATION

This application claims benefit of provisional application Ser. No. 61/315,964 filed Mar. 21, 2010 whose contents are included herein by reference.

FIELD OF THE INVENTION

This invention relates to a device or system and method for the delivery of fluids or gels by injection into or underneath the human skin for wrinkle treatment or for other purposes.

BACKGROUND OF THE INVENTION

A wide range of subcutaneous drug delivery devices is known.

Several years ago the needs of society in the medical field were different from today's needs and the technology abilities then were also different from modern technology. In the 1950's there was a very big need to treat diabetes mellitus with self-administered insulin injections. These needs were met by several devices, whose purpose was to allow a person to administer self injections of the drug at home. Such devices are disclosed, for example, by U.S. Pat. No. 2,660,169 titled "Devices for supporting and operating hypodermic syringes and injecting a fluid into the body". The device is very simple, with no electronics in it, operated by manual pressure only. Its only function is to inject the whole contents of the syringe at once into the patient.

Later, in the 1970's another need arose—to vaccinate a large population in a short period of time. This need was addressed by "gun-like" injection devices, such as disclosed in U.S. Pat. No. 3,727,614, which discloses a multiple dosage inoculator for administrating vaccines, where the vacuum is used to draw the skin of the patient onto the needle using only one hand.

Another "gun-like" injection device adapted for the self-injection of insulin is disclosed in U.S. Pat. No. 4,067,334. This device is manually operated. The syringe is connected to a spring, that allows its movement, and a drug is injected by releasing the air pressure contained in the bulb, operated by the user.

Another field of the medicine/cosmetic treatments that was developed around the 1980's is mesotherapy. U.S. Pat. No. 4,108,177 discloses a gun-like device, operated by an electromagnet and a motor. This is the first invention that uses an electric mechanism to create motion. The device is able to perform many injections in a short period of time, and create very fast syringe motion and very fast fluid injection.

U.S. Pat. No. 4,512,767 discloses a gun-like mesotherapy mechanical injection device, which includes means for positioning the penetration needle and to predetermine the degree of penetration of the needle.

U.S. Pat. No. 4,790,823 discloses another such device having an optical sight for a precise needle direction and a microcontroller for controlling the quantity of the injected fluid and the speed of injection.

U.S. Pat. No. 4,600,403 discloses a suction injector where an electric motor is used to create suction. The injection is triggered by the skin, as soon as it has been raised high enough and the amount of injected fluid is electronically controlled.

In U.S. Pat. No. 4,833,384 a motor is coupled to a lead screw that moves a syringe plunger whose position is accurately controlled by a digital encoder.

A very important factor in automatic injection devices is the need to control needle penetration depth. One solution is taught by U.S. Pat. No. 5,015,235 where the user selects an adjuster from a set of adjusters of different sizes and fits it over a part of a hub.

U.S. Pat. No. 5,690,618 discloses an electronic syringe for administrating anesthetic injections, particularly suited in dental applications where a precise level of hand control is required. A drive means is provided in electrical communication with an electronic controller, which controls the amount of the injected fluid and the injection flow rate.

U.S. Pat. No. Re. 35,986 discloses an automatic injector having two chambers containing different ingredients of medicament separated by a membrane and mixed during injection. Needle penetration depth is limited by placing a disc on the needle.

U.S. Pat. No. 5,906,592 discloses a device for accurately infusing fluids into a patient at specific rates over an extended period of time.

U.S. Pat. No. 5,921,962 discloses an injection device having a flow indicator that provides an indication at any given time about the amount of fluid remaining in the device.

U.S. Pat. No. 6,994,691 discloses an injection device for making injection at a predetermined depth in skin. A skin positioning member is positioned on a patch of skin within an area of skin such that at least a part of the patch of skin may be held elevated above or depressed below the area of skin. A guidance mechanism guides an injection needle to slide beneath the skin positioning member to an injection position.

As it can be seen in the prior art study, known injection devices are able to penetrate the skin perpendicularly, but they cannot perform a series of injections while controlling the distance between those injections; neither can they control the needle penetration speed. For all the reasons listed above, filler injection procedures are being performed manually.

The problem of the filler's manual injections methods used in today's practice is that the needle penetration is done in parallel to the skin surface. In that way consequently, it is very difficult to control the injection depth accurately and to control the amount of the injected drug/filler. Moreover, it is difficult or impossible to maintain the layer of the injected drug/filler under the skin surface uniform without lumps. Additionally, the procedure is painful owing to internal skin tissue tearing and patient bleeding due to the blood vessels injury. Also, it is difficult to avoid swelling, pain and redness following treatment.

Additionally, it emerges from the prior art review that there is a need for an advanced injection device able to control the speed of needle penetration into the skin. There is a need for the device to be able to control the depth of needle penetration, injection flow rate, and the volume of the injected fluid or gel.

There is a need for the device to be painless, able to perform a series of injections, to control the distance between those injections, and to be capable of computer control or/and manual control.

The present invention overcomes the disadvantages of the injection devices associated with prior art drug delivery devices, the disadvantages of the devices existing on today's market and the disadvantages of manual injecting of drugs or fillers.

SUMMARY OF THE INVENTION

In accordance with the invention there is provided a device for successively injecting material at predetermined distances between successive injections to body tissue along a desired path of skin surface, said device comprising:

an injector sub-assembly having a needle configured for injecting said material into body tissue, and a displacement sub-assembly configured to facilitate precise displacement of the needle or of the device along said path between successive injections.

The invention thus principally resides in a device that is adapted to inject a needle into a surface of the skin to a required depth of penetration for injecting a required amount of material and which is adapted to move the needle by a required displacement between successive injections.

According to this invention there is provided a device or system and method of delivery of fluids or gels by injection into or underneath the epidermis layer, or into or underneath the dermis layer of human beings.

The device allows injecting the fluid or gel to a predetermined, settable or controllable depth under the skin surface either for wrinkle treatment or for other purposes thus avoiding blood vessels injury.

The device allows the treated skin area to be subjected to a series of injections along a desired path at a predetermined, settable or controllable distance between the injections. The device also allows a predetermined, settable or controllable amount of fluid or gel to be injected in each injection, thereby achieving a uniform layer of fluid or gel. The device further allows injecting the fluid or gel at a predetermined, settable or controllable flow rate.

The injection needle is very thin (32 G and above) in order to minimize the injury to the patient's skin.

In some embodiments, the device allows the speed of needle penetration into the skin to be predetermined, settable or controllable speed thus allowing use of very thin needles (32 G and above).

In some embodiments, the device may be used to inject one of the currently available fillers for wrinkle treatment. The device includes a thin needle attached to either a syringe or to a container, containing the fluid or gel to be injected.

In some embodiments, the injections can be carried out by a needle, or alternatively by a group of two or more needles linked to the fluid/gel syringe or container.

In some embodiments, the device includes a mechanism, which controls the injecting mechanism movement and the speed of needle penetration into the skin. The device includes another mechanism whose purpose is to limit or set the needle's penetration depth beneath the skin surface.

In one embodiment, the device includes a mechanical stopper, which stops the needle penetration once it touches the skin surface.

Alternatively, a mechanical end-stop may be mounted on the needle in fixed spatial relationship with an end thereof. For example, a disc may be mounted on the needle to limit the depth of needle penetration into the skin.

In some embodiments this mechanism is based on a sensor or micro-switch, that detects contact with the skin surface once the needle has penetrated a desired depth beneath the skin surface, and stops the needle insertion.

In some embodiments, a muzzle surrounds the needle and a vacuum source draws the patient's skin into the muzzle in order to perform the injection.

The device includes a mechanism for pushing the liquid or gel contained in the syringe or the container, so when this mechanism is activated, the liquid or gel is injected through the needle into the treated area. This mechanism is able to inject a predetermined, settable or controllable amount of fluid or gel at a predetermined, settable or controllable flow rate in each injection.

In some embodiments, the device indicates the user about the amount of fluid or gel containing in the syringe or container.

The device includes a mechanism, which causes the device to advance a predetermined, settable or controllable distance between injections.

In some embodiments, the user directs the device along the desired treatment path (along a wrinkle for instance) manually, using a mechanical or optical pointer attached to the device.

Alternatively, the device is capable to move forward automatically along the treatment path without external manual interaction by the user.

In some embodiments, the device includes an optical sensor such as a camera, connected to an external TV set, screen or computer, so the image captured by the optical sensor can be seen on the screen. This allows the operator to direct the device more precisely.

In some embodiments, the desired treatment path is dictated by using an optical sensor. The device controller controls the advancement direction of device by analyzing the data received from the optical sensor in such a way that the device follows and treats the desired treatment path, such as a skin wrinkle.

In such an embodiment the device is capable to move forward along the desired treatment path automatically.

In some embodiments, the device comprises a light source, such as, but not limited to, one or more LED's located close to the needle or the injection place in order to improve visibility of the treated area by the person carrying out the treatment.

In some embodiments, the device includes a massaging mechanism for massaging the already treated skin area. The massaging mechanism is located behind the syringe and the needle, so that each time it is activated, it massages a different treated skin area along the treatment path.

In some embodiments, the user can manually select the device operation mode according to the needed treatment. For instance, for wrinkle filling the user may select shallow, medium or deep wrinkle setting. The device controller sets the injection filler quantity to be injected each time, the needle's penetration depth, the distance between consecutive injections and the massaging session duration according to the selected setting.

In some embodiments, the user can manually select the flow rate of the gel or fluid according to the needed treatment.

In some embodiments the device controller analyzes the data received from an optical, electronic or mechanical sensor, estimates the wrinkle depth and sets accordingly the injection filler quantity to be injected each time, the injecting flow rate, the needle's penetration depth, the distance between consecutive injections and the massaging session duration.

In some embodiments, the device includes a mechanism which allows also a widthwise motion of the described above mechanism, so a skin area can be treated by applying a matrix-like pattern of injections rather than a linear path of injections.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Mechanical System Description

Figure 1:
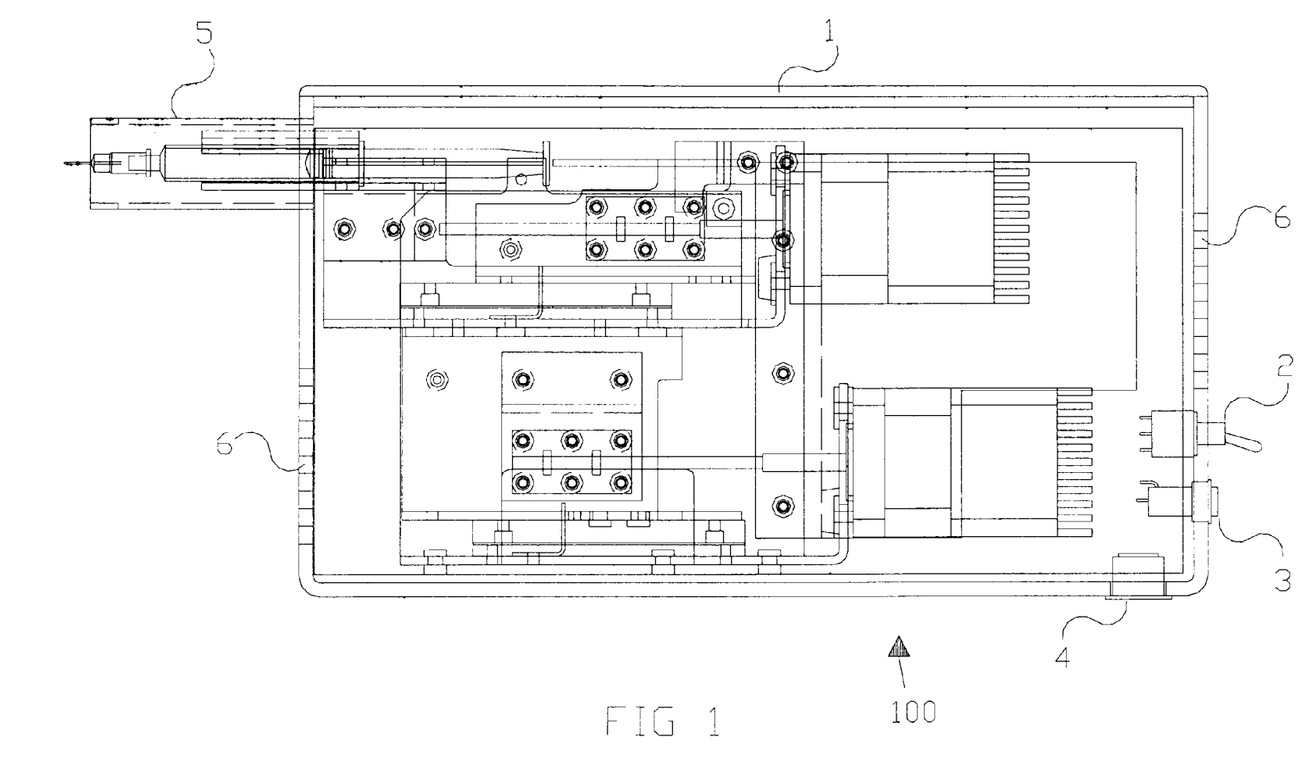
FIG. 1 is a schematic view showing the principal sub-assemblies in a device according to the invention.
Figure 2:
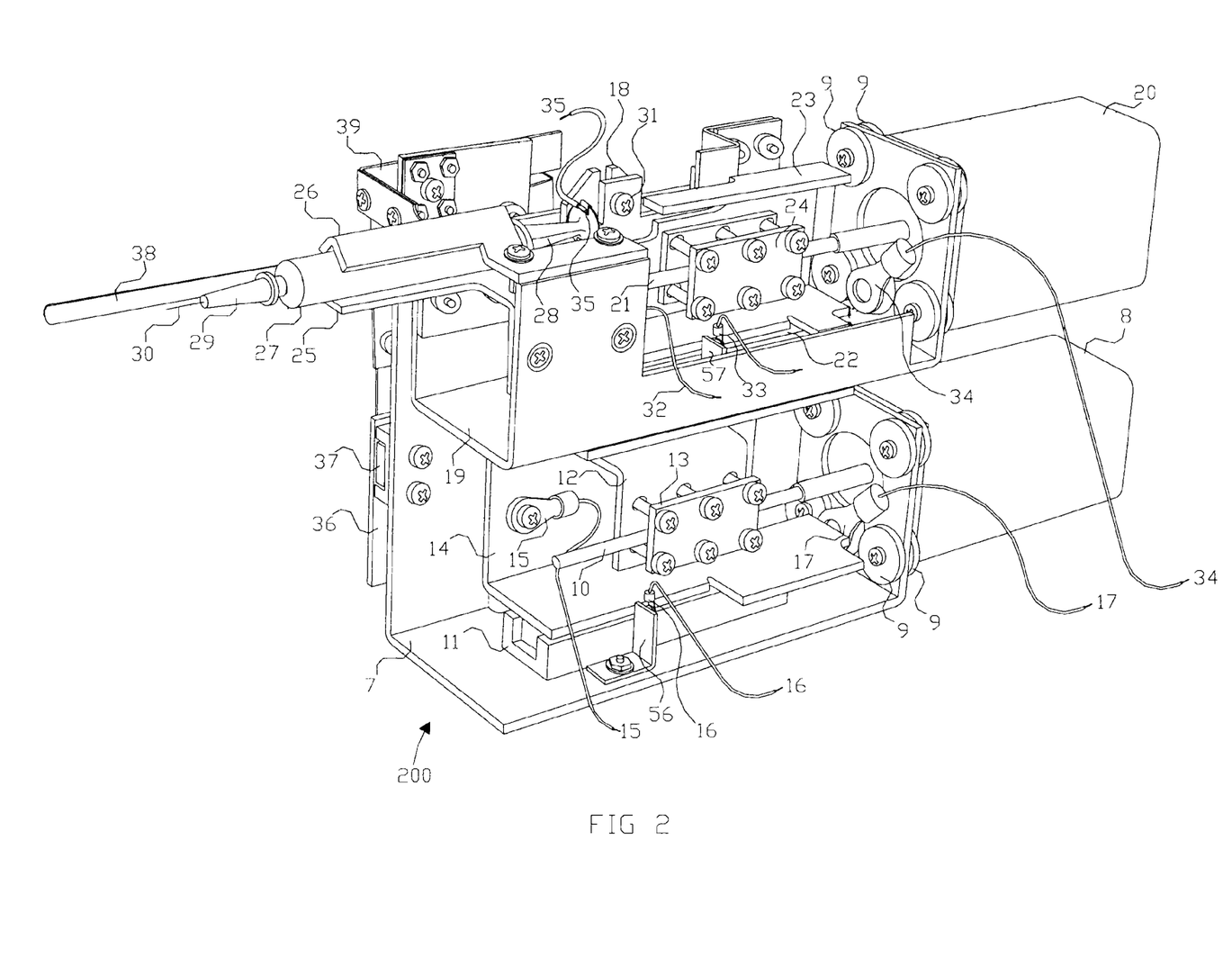
FIG. 2 is a perspective view of a base sub-assembly and injector sub assembly with a syringe mounted in its place.
Figure 3:
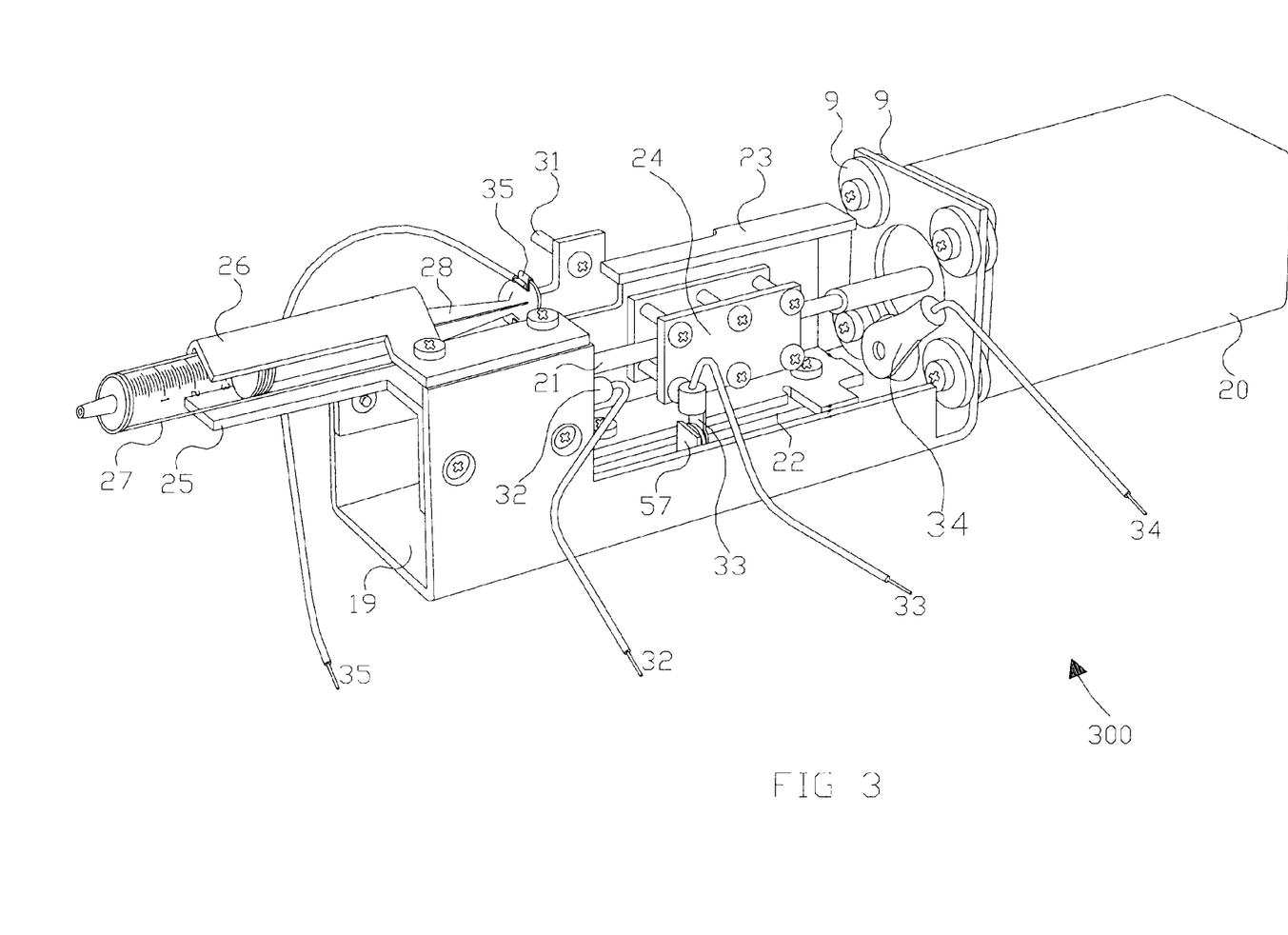
FIG. 3 is a perspective view of the injector sub-assembly.
Figure 4:
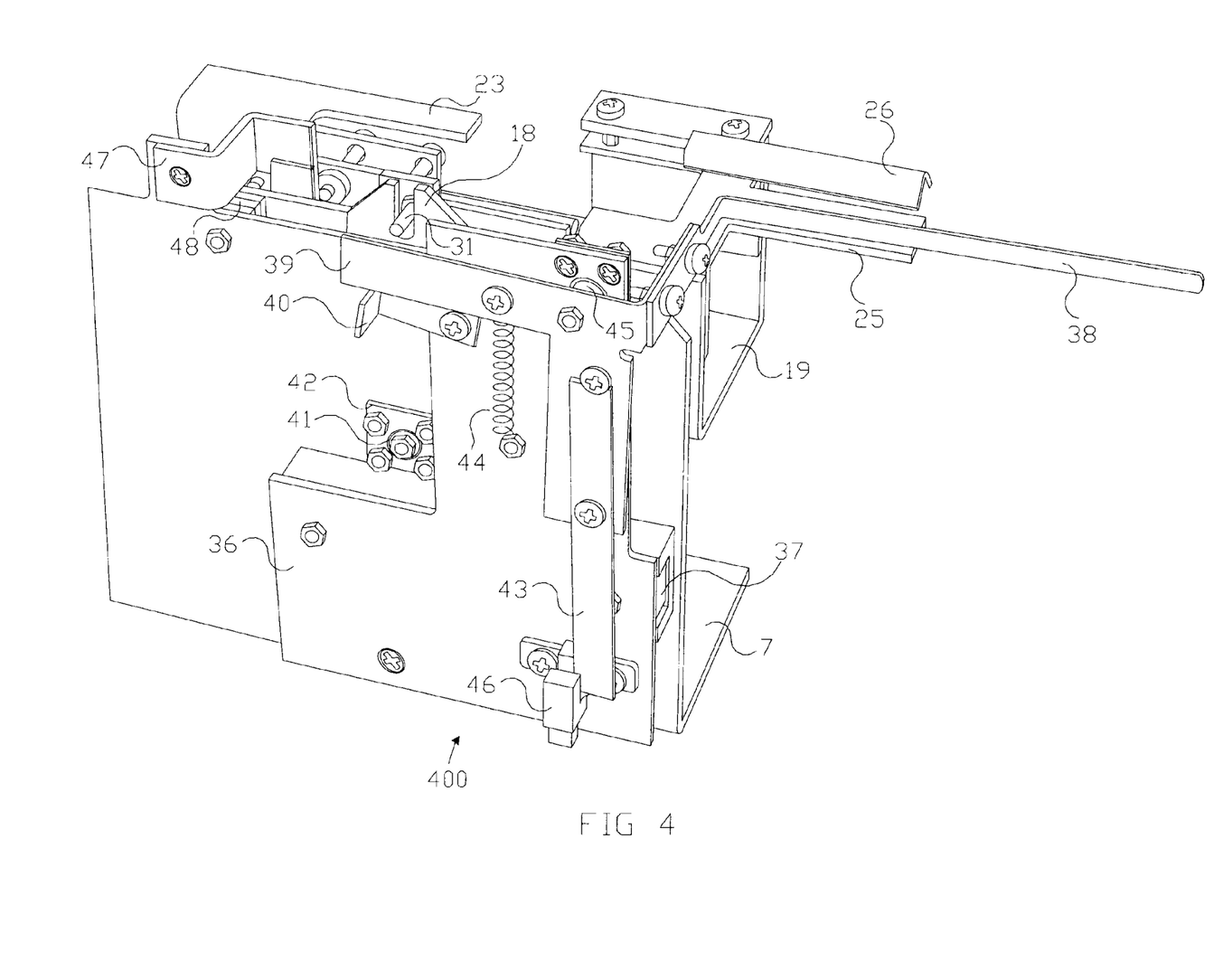
FIG. 4 is a perspective partial view of the device showing in greater detail the displacement control sub-assembly.

FIG. 1 shows schematically a device 100 according to the invention comprising four sub-assemblies, namely an enclosure 1, a base 200 shown in FIG. 2, an injector sub-assembly 300 shown in FIG. 3 and a displacement control sub-assembly 400 shown in FIG. 4. The base sub-assembly 200 serves to move an injection needle 30 into close proximity to the skin being treated and to advance the needle to a controlled depth of penetration. The injector sub-assembly 300 serves to inject a controlled amount of material into or beneath the skin. The displacement control sub-assembly 400 is adapted to operate only when the injector sub-assembly 300 is retracted (so that the needle is withdrawn) and serves to advance the device a controlled distance along the skin prior to the next injection of additional material.

The enclosure 1 is in the shape of a box from one side of which there protrudes a transparent polycarbonate pipe 5. In order to start the treatment, the transparent pipe 5 is perpendicularly placed in contact with the treated person's skin 51 (shown in FIG. 7a) directly over an area to be treated (typically a wrinkle). By doing this, the base 200 is located at the correct distance from the treated person's skin 51. The pipe 5 thus constitutes a safety stop that at least partially surrounds the end of the needle and prevents inadvertent penetration thereof. The enclosure 1 further comprises an on-off switch 2, a power connector 3 for allowing connection of the unit to an external power supply, a data connector 4 for allowing connection of the unit to a computer and ventilation openings 6.

The function of the base 200 is to support and drive the injector 300 and the displacement control unit 400, as well as to support an electronic circuit by means of which the device is controlled.

Figure 5A:
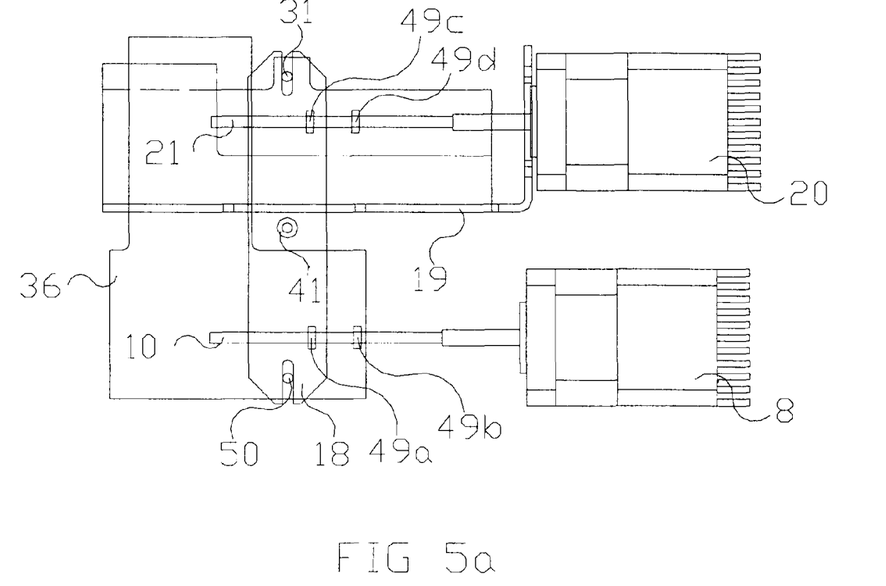
FIGS. 5a and 5b show details of a linkage that induces relative movement between the injector sub assembly and the displacement control sub-assembly.
Figure 5B:
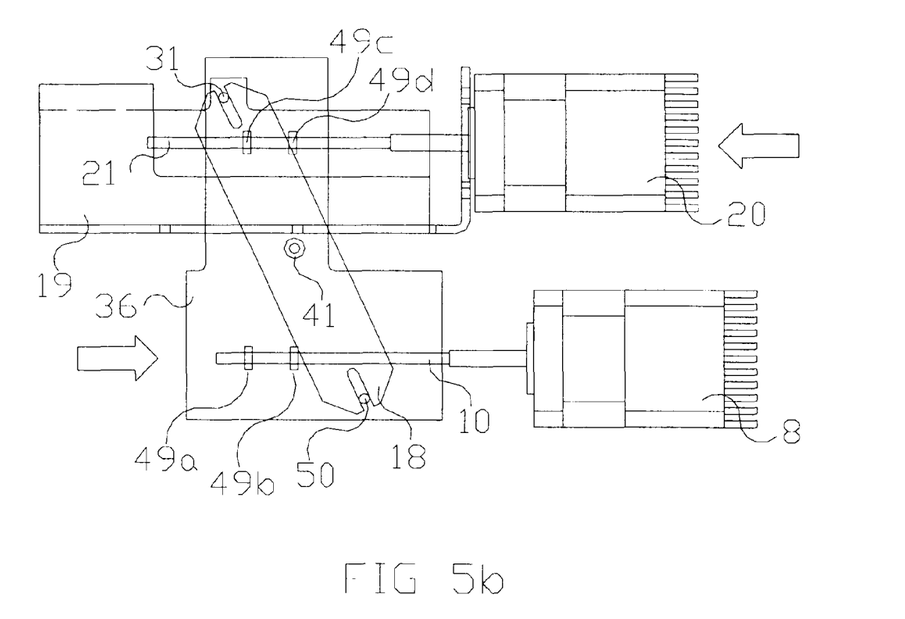
Figure 6:
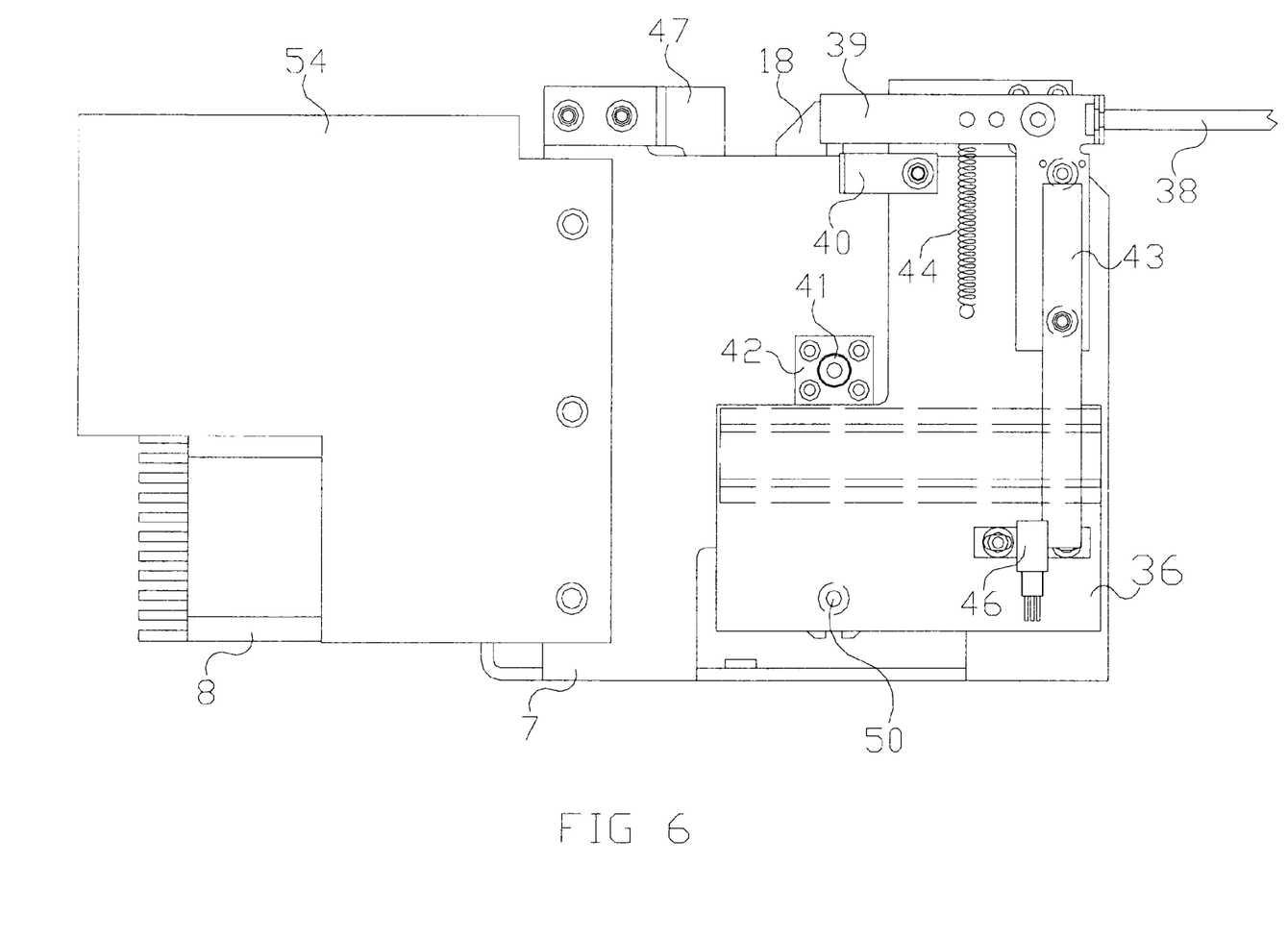
FIG. 6 is a detailed view of the displacement control sub-assembly and the electronic printed circuit board.

The base 200, which is fixed to the enclosure 1, includes a base plate 7 that is folded at two adjacent edges to form first and second mutually perpendicular support surfaces that are each perpendicular to the base plate 7, the first at an end thereof for supporting a stepper motor 8 (constituting a first drive unit) and the second at a side thereof for supporting a linear bearing 37. A shaft of the stepper motor 8 is coupled to a screw rod 10, which threadably engages a pair of nuts 49a and 49b (shown in FIGS. 5a and 5b), fixed to a carriage 14 that supports the injector sub-assembly 300 so that rotation of the motor shaft induces linear motion of the injector. The carriage 14 is slidably supported within a linear bearing 11 fixed to the base plate 7 and comprises nut holders 12 and 13, an electrical contact 15 and it supports an injector base plate 19. The base plate 7 also supports, a linear bearing 37 slidably supporting the displacement control unit 400, a rotary bearing 41 (shown in FIG. 4) supporting a lever 18, an electronic PCB 54 (shown in FIG. 6) and two electrical limit switch contacts 16 and 17.

The attachment of the stepper motor 8 to the base plate 7 allows for a limited amount of flexibility, achieved through rubber discs 9. This compensates for slight inaccuracies and misalignments without creating distortion of mechanical parts or causing stress or friction between the screw rod 10 and the nuts 49a and 49b during rotation of the stepper motor 8.

When the stepper motor 8 rotates, it moves the nuts 49a and 49b, which are supported by the nut holders 12 and 13, consequently shifting the carriage 14 supporting the injector sub-assembly 300 along the screw rod 10. The extent of this movement is limited: at the retracted "home" position, a contact 15 fixed to the carriage and constituting a moving contact 14 makes electrical contact with the switch contact 17, which is mounted on a rubber isolator glued to the base plate 7 thus closing an electrical switch comprising contacts 15 and 17. At the extended "end of travel" position, the carriage 14 makes electrical contact with the switch contact 16, which is mounted on a rubber isolator glued to a bracket 56 fixed to the base plate 7 thus closing an electrical switch comprising contacts 15 and 16. In this way, the stepper motor 8 can be controlled to move within its movement range without exceeding it. Rotating the stepper motor 8 in a clockwise direction will move the injector sub-assembly towards its extended "end of travel" position, while rotating it in a counter-clockwise direction will move the injector sub-assembly towards its retracted "home" position.

Injector aligners 47 and 48 (shown in FIG. 4) allow the injector sub-assembly 300 mounted on the carriage 14 to move linearly along its path, thereby avoiding any undesired moment in the linear bearing 11 due to lateral forces such as the injector weight.

During normal operation the injector sub-assembly 300 is periodically moved from its "home" position towards its "end of travel" position, without reaching it, and back to the "home" position.

During the movement towards the "end of travel" position, a needle 30 supported by the injector sub-assembly 300 is inserted a predetermined depth into the skin 51. The length of the transparent pipe 5 in the enclosure is such that when the needle 30 is in its inserted position, the "end of travel" position is not yet reached. The "end of travel" contact 16 provides a security means for avoiding mechanical overdrive of the carriage 14 within the linear bearing 11 beyond its permitted range of movement.

As can be seen in FIGS. 2, 3, 4 and 5, a pin 31 protrudes outward from a side surface of the injector sub-assembly 300 and engages an upper slot within a lever arm 18 that is pivotally mounted by a rotary bearing 41, which is fixed to the second surface at the side of the base 7. In similar manner, a lower slot in the lever arm 18 engages a pin 50 that protrudes outwardly from the displacement control sub-assembly 400. Pin 50 is attached to a support plate 36 that is slidably supported within the linear bearing 37, which is fixed to the second surface at the side of the base 7. As the injector sub-assembly 300 moves in a first direction within the linear bearing 11, the pin 31 induces rotation of the lever arm 18 thereby causing the displacement control sub-assembly 400 to move in the opposite direction as shown in FIGS. 5a and 5b. In this way, when the injector sub-assembly 300 is extracted towards the skin 51 in order to inject, the displacement control sub-assembly 400 is retracted backwards away from the skin 51, and when the injector sub-assembly is retracted backwards towards its "home" position, the displacement control sub-assembly 400 is extracted towards the skin 51.

The injector sub-assembly 300 serves to support a syringe 27 (constituting a container for storing a reservoir of material) and to shift a piston 28 therein, which is pushed in such way that a precise amount of the syringe's contents is injected into the treated skin 51 at a precise flow rate during each injection while allowing the needle 30 to penetrate the skin 51 to a precise, predetermined depth.

As seen best in FIG. 3, the injector sub-assembly 300 comprises a base 19 supporting mutually perpendicular opposing side support surfaces and an end support surface. Mounted on the end support surface is a stepper motor 20 (constituting a second drive unit) whose shaft is coupled to a screw rod 21. The syringe 27 is supported within opposing syringe holders 25 and 26 protruding from an end of the base 19 opposite the stepper motor 20. A piston shifter 23 is slidably supported within a linear bearing 22 mounted on the base 19 and supports a nuts holder 24. Nuts 49c and 49d (shown in FIGS. 5a and 5b) fixed to the nuts holder 24 are threadably supported on the screw rod 21 so that rotation of the stepper motor 20 induces linear movement of the piston shifter 23. The piston shifter constitutes a release unit operable by the second drive unit for releasing a desired quantity of material from the container.

The extent of this movement is limited. At the retracted "home" position, the piston shifter 23 makes electrical contact with the switch contact 34, which is mounted on a rubber isolator glued to the injector's base plate 19 proximate the stepper motor 20, thus closing an electrical switch comprising the contact 34 that is fixed to the base plate 19 and a contact 32 that is fixed to the piston shifter 23. The piston shifter 23 is formed of electrically conductive material and is electrically coupled to the switch contact 32. At its extended "end of travel" position, the piston shifter 23 makes electrical contact with a switch contact 33, which is mounted on a rubber isolator glued to the end of travel contact holder 57, thus closing an electrical switch comprising contacts 32 and 33. In this way, the stepper motor 20 can be controlled to move the piston shifter 23 within its movement range without exceeding it. Rotating the stepper motor 20 in a counter-clockwise direction will move the piston shifter 23 towards its retracted "home" position, conveniently allowing the user to install the syringe 27 in its place and to secure it by tightening the screws that hold the syringe holder 26. Rotating the stepper motor 20 in a clockwise direction will move the piston shifter towards its extended "end of travel" position, advancing towards the syringe's piston 28. Once the piston shifter 23 reaches the piston 28, it makes electrical contact with the switch contact 35, which is mounted on the piston thus closing an electrical switch comprising the contact 35 and a contact 32 that is fixed to the piston shifter 23. This allows the stepper motor 20 to be controlled to quickly advance the piston shifter 23 until it reaches the piston 28, and afterwards to move forward slowly injecting a precise amount of the syringe's contents into the treated skin 51 at a precise, controlled flow rate.

The "end of travel" contact 33 is located in such position that the piston shifter 23 will reach and make contact with it a short distance before the syringe's piston 28 reaches the end of the syringe 27, thus avoiding mechanical overdrive of the piston shifter 23. This contact may also serve as an "Empty Syringe" alarm activation signal.

Figure 7A:
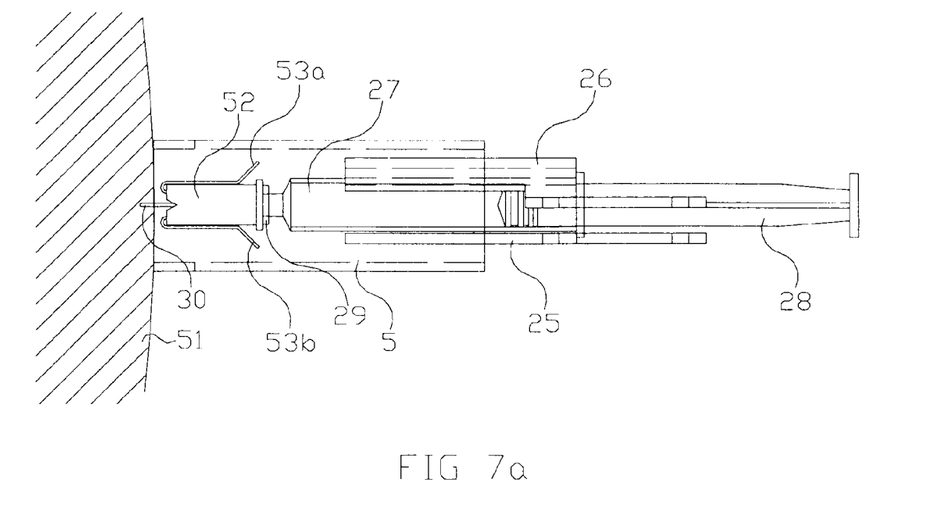
FIG. 7a is a partial detailed view of the device in use.
Figure 7B:
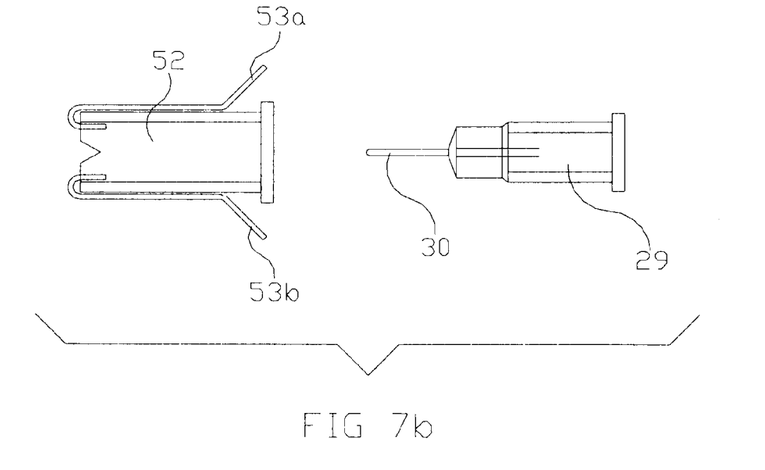
FIG. 7b shows detailed views of the needle and the injection depth limiter when separated.

An injection depth limiter as depicted in FIGS. 7a and 7b is provided. The injection depth limiter's role is to enable the control of the injector's movement while the needle 30 is inserted into the skin 51, so it penetrates the skin 51 down to a precise, controlled depth.

FIG. 4 shows in greater detail the displacement control sub-assembly 400, which comprises a generally L-shaped advancement lever holder 39 pivotally mounted on bearing 45 and urged into a rest position where it engages a limiter 40 by a spring 44. As explained above with reference to FIGS. 5a and 5b, the displacement control sub-assembly 400 is articulated to the injector sub-assembly 300 by the lever arm 18 so that when the injector sub-assembly 300 is retracted away from the skin, the displacement control sub-assembly 400 is moved toward the skin. When this happens, an advancement feeler lever 38 attached to a horizontal portion of the advancement feeler lever holder 39 is brought into contact with the skin 51. In addition to that an electrical circuit provides an audible "beep" for alerting the user that the injection needle is withdrawn and prompting him or her to manually move the device along the treatment path to the next location for a subsequent injection.

Downward movement of the device along the treatment path while the advancement feeler lever 38 is in contact with the skin 51 induces clockwise rotation of the displacement control sub-assembly 400 about the bearing 45, causing the advancement lever holder 39 to rotate clockwise and to be raised above the limiter 40 against the biasing force of the spring 44. Rotation of the displacement control sub-assembly 400 also causes a lever 43 fixed to the vertical portion of the advancement lever holder 39 to rotate so that a lower end of the lever 43 is brought into the path of an optical sensor 46. When this happens, circuitry coupled to the optical sensor 46 is adapted to provide another audible "beep" for alerting the user that the device is now located at the correct position for the next injection and prompting him or her to stop downward movement of the device. In actual use, the device is oriented so that the spring 44 is substantially parallel to the treatment path.

As the device is advanced along the path to be treated and advancement lever holder 39 moves, the spring 44 is further extended. When the device has reached the position for the next injection, the injector sub-assembly is extracted thus retracting the displacement control sub-assembly 400 owing to their interconnection via the lever arm 18. When the advancement feeler lever 38 loses its contact with the skin 51, the spring 44 returns the advancement lever holder 39 to its rest position. This rest position is determined by the limiter 40 position, which is adjustable. Once the advancement lever holder 39 and the advancement feeler lever 38 are back in their rest position, the device is ready for the next cycle.

The position of the lever 43 is adjustable such that the distance it has to travel before intercepting the optical sensor 46 can be varied. In this way the distance between consecutive injections can be set. In another embodiment, this adjustment may include a small motor, or any other means to enable control of the distance between consecutive injections once the device is activated, or while the device is operating.

The displacement control sub-assembly 400 serves to allow for a predetermined distance between consecutive injections along the treated path.

In the embodiment shown in the figures, the device is advanced along the treatment path manually, while the person holding the device is alerted when the device has to be shifted, and when movement of the device has to be stopped as it has reached the position for the next injection. In this way a predetermined distance between consecutive injections is achieved. In other embodiments, the device may include a motor or any other mechanical provision for moving the device a predetermined distance between consecutive injections.

FIGS. 7a and 7b show details of an injection depth limiter having two mutually insulated contacts 53a and 53b which are supported by a plastic electrically insulating tube 52, of complementary shape to a base 29 of the needle 30, so that when mounted on the needle's base 29 the contacts 53a and 53b are always at the same distance from the end of the needle. In this way when the needle 30 penetrates the skin 51 to the correct depth, both contacts 53a and 53b touch the skin 51. The contacts 53a and 53b detect skin conductivity between them and serve as a skin sensor by means of which the electronic circuit shown in FIGS. 8a and 8b sends a signal to the controller within motor 8 and controller stops the needle's insertion into the skin, thus achieving a precise depth of injection. Furthermore, the plastic tube 52 not only supports the contacts 53a and 53b, but also has the mechanical role of physically limiting the injection depth, ensuring improved safety for the treated person.

FIG. 7b shows in enlarged scale a detail of the depth limiter and the needle prior to engagement. A "V" shaped bore in the end of the plastic tube 52 intermediate the two contacts 53a and 53b, serves to avoid the unwanted creation of a continuous wet pattern between the two contacts which might result in a residual conductance that would jeopardize the correct operation of the depth limiter.

In the embodiment shown in the figures, the insertion depth is fixed depending on the geometry of the injection depth limiter, but it is possible to implement other embodiments, which use a different kind of injection depth limiter so the injection depth will be controllable during the operation of the device. Other embodiments may use an injection depth limiter based only on mechanical components.

Figure 8A:
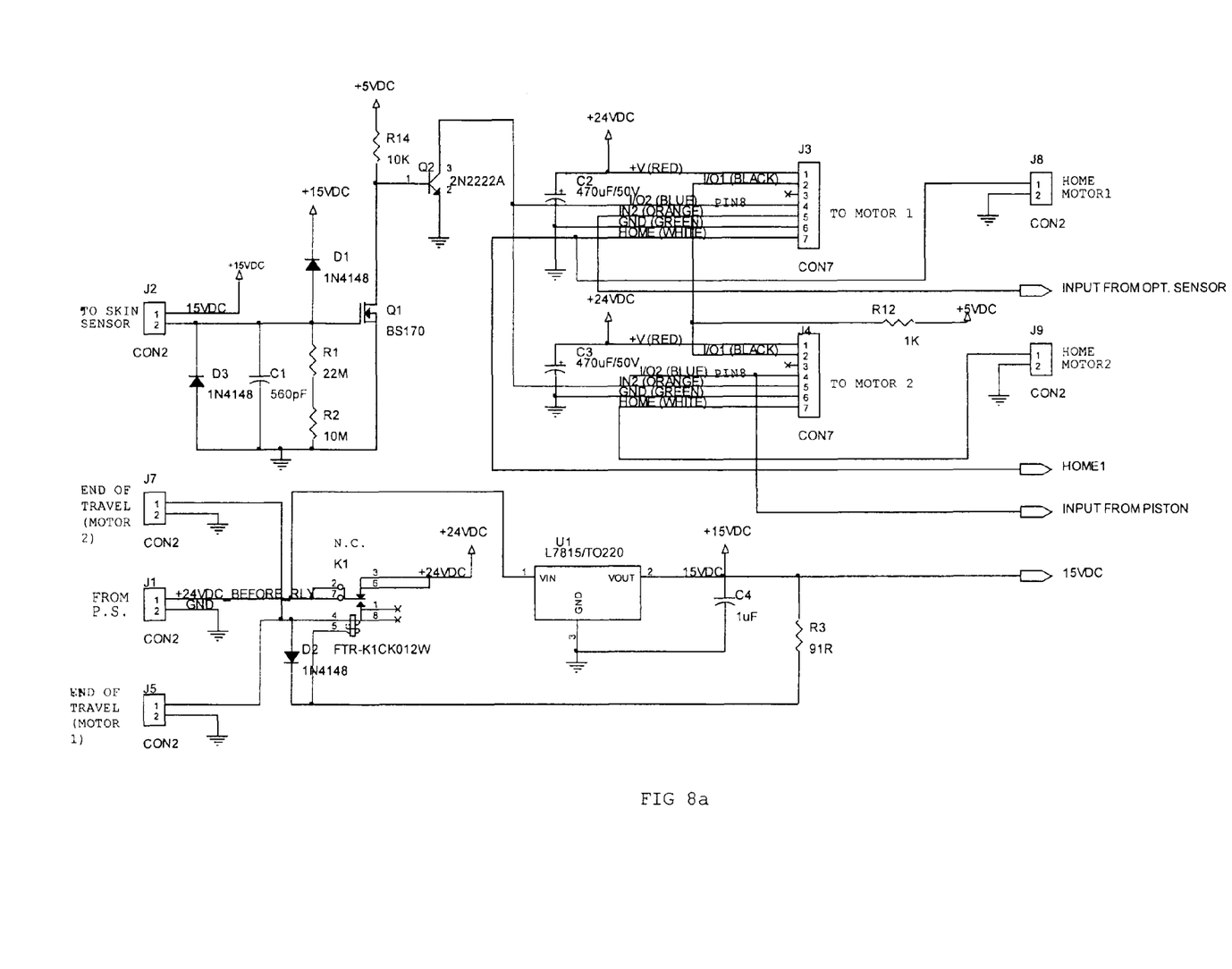
FIGS. 8a and 8b is a schematic diagram of an electronic circuit used to control the device.
Figure 8B:
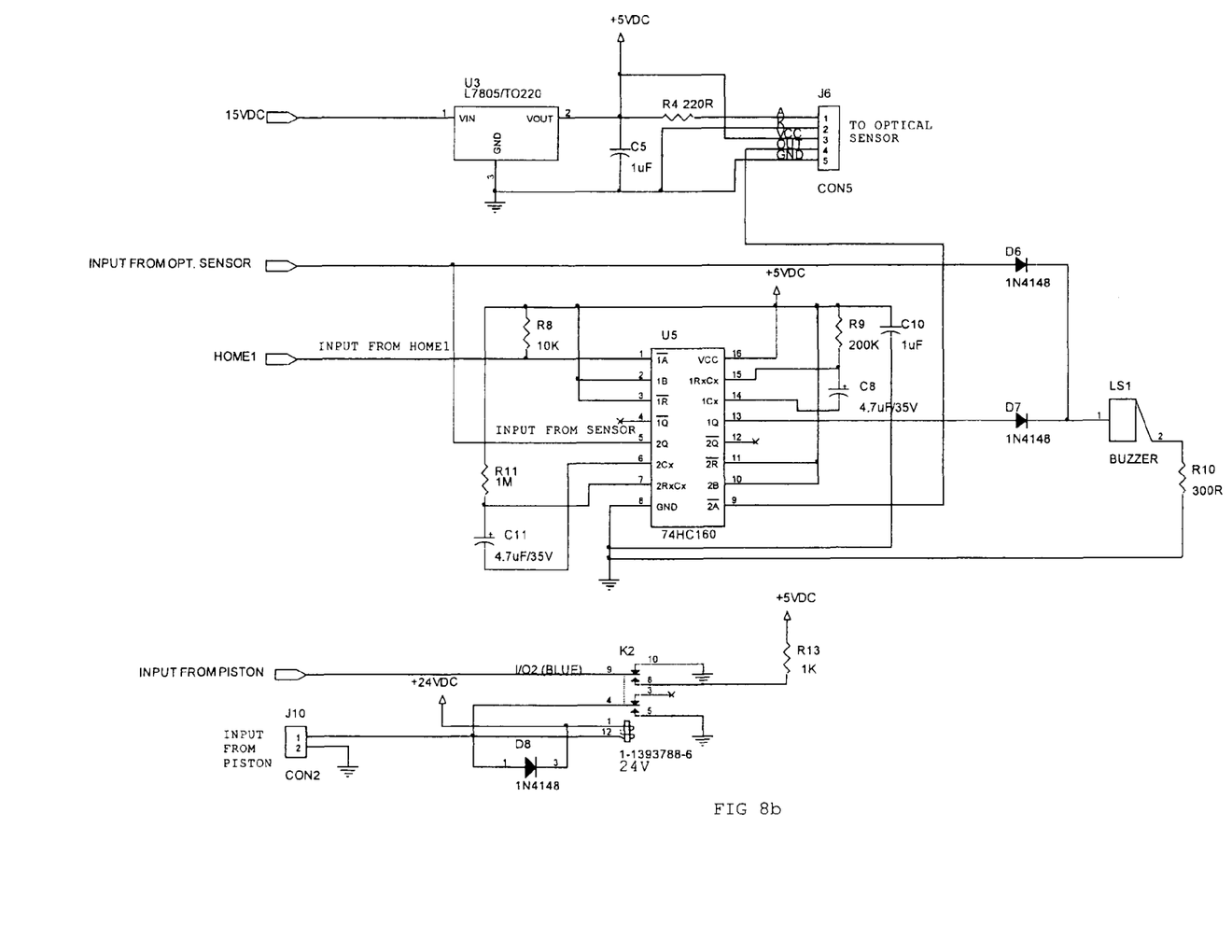
Figure 9A:
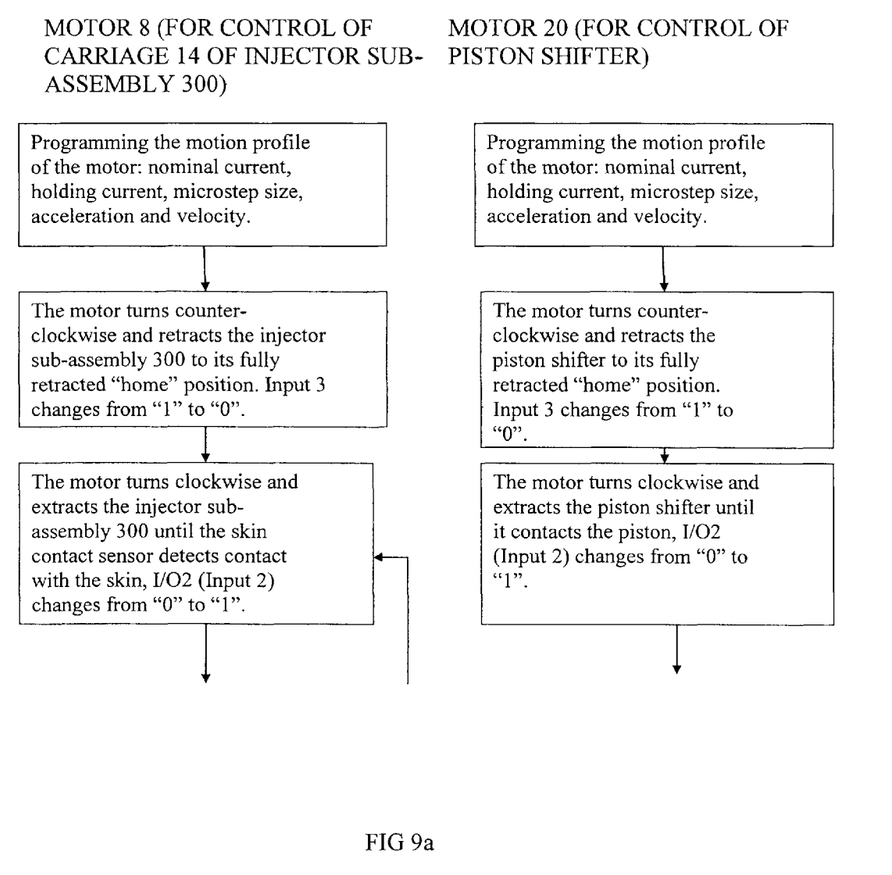
FIG. 9 is a flow diagram showing the principal operations carried out during operation of the device.
Figure 9B:
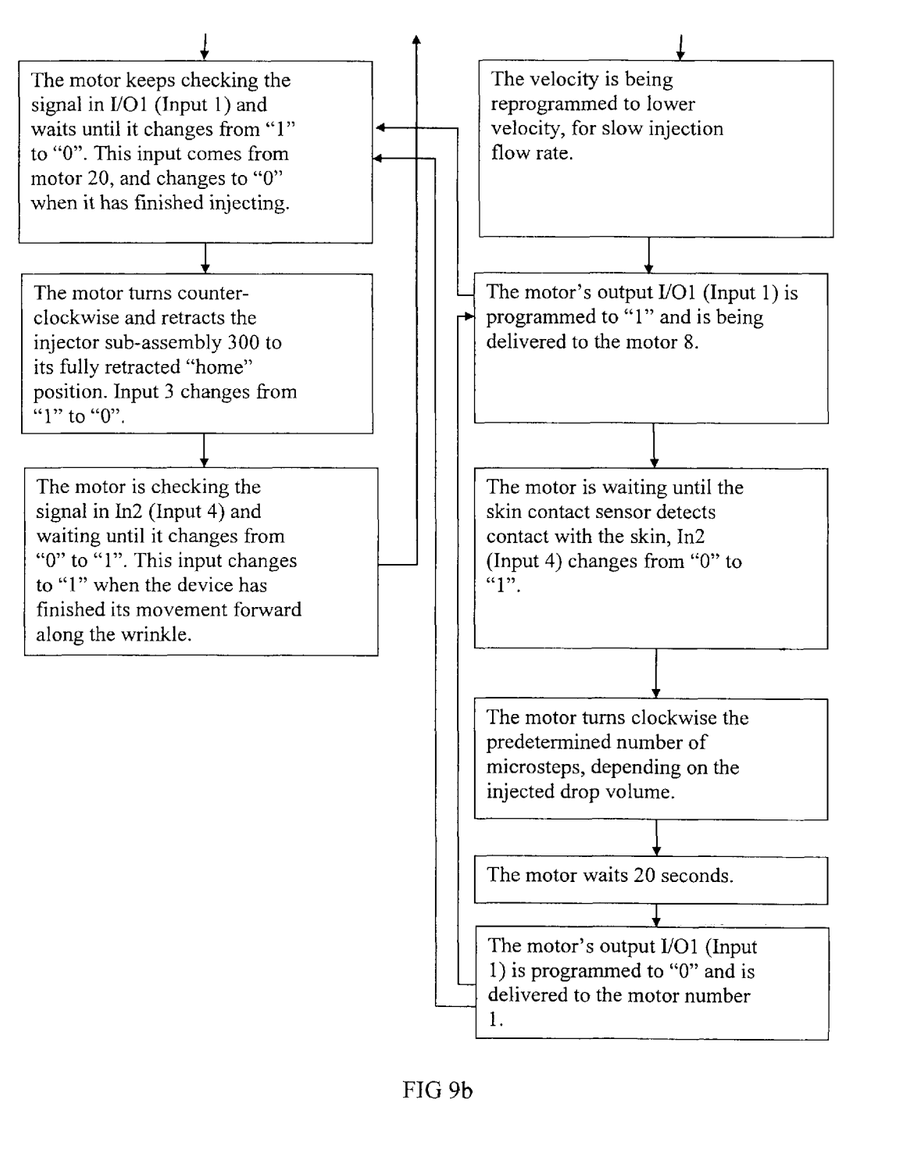

Operation of the device during actual use will now be described with reference to the schematic circuit diagram shown FIGS. 8a, 8b and the flow chart shown in FIGS. 9a, 9b.

Operation of Motor 8 for Control of Carriage 14 of Injector Sub-Assembly 300:
1. A user programs the motion profile of the motor 8: nominal current, holding current, microstep size, acceleration and velocity.
2. The motor 8 turns counter-clockwise and retracts the injector sub-assembly 300 to its fully retracted "home" position. When the injector sub-assembly 300 reaches this position, it touches the limit switch contact 17, thereby shorting pins 1 and 2 of connector J8, and as a result input 3 fed to connector J3 pin 7 changes from "1" to "0". Additionally, the same signal enters pin 1 of U5 (74HC160) and, as a result, the user hears one short buzzer beep.
3. The motor 8 turns clockwise and extracts the injector sub-assembly 300 until the contacts 53a and 53b of the skin sensor detect contact with the skin. The skin contact sensor is connected to a connector J2 a first of whose pins is at positive potential and to a second of whose inputs a transistor Q1 is connected, such that Q1 starts conducting only when the sensor is contacting a skin surface. When Q1 conducts, transistor Q2 is likewise biased into conduction and a signal I/O2 fed to pin 4 of connector J3 changes from "0" to "1".
4. The motor 8 keeps checking the signal I/O1 at pin 2 of connector J3 and waits until it changes from "1" to "0" when the motor 20 has finished injecting.
5. The motor 8 turns counter clockwise and retracts the injector sub-assembly 300 to its retracted "Home" position. When the injecting mechanism reaches its retracted position, it contacts the switch contact 34, thereby shorting pins 1 and 2 of connector J8. As a result an input 3 fed to pin 7 of connector J3 changes from "1" to "0". In addition, the same signal is fed to pin 1 of U5 (74HC160) and, as a result, the user hears one short buzzer beep. This short beep is a sign for a user to advance the device along the treated path.
6. The motor 8 checks the signal IN2 fed to pin 5 of connector J3. A user moves the device forward along the wrinkle. When the device has advanced sufficiently, the signal at pin 4 of connector J6 changes from "1" to "0". This signal is fed to pin 9 of U5 (74HC160). As a result two things occur: the user hears a long buzzer beep and stops the device advancing; and the signal at pin 5 of connector J3 changes from "0" to "1". When this input changes to "1", the motor's processor knows that the device had finished its movement forward along the wrinkle
7. After step 6 the program jumps again to step 3.

Operation of Motor 20 for Control of Piston Shifter
1. Programming the motion profile of the motor 20: nominal current, holding current, microstep size, acceleration and velocity.
2. The motor 20 turns counter-clockwise and retracts the piston shifter 23 to its fully retracted "Home" position, where it contacts the switch contact 34. As a result pins 1 and 2 of connector J9 are shorted, and input 3 fed to pin 7 of connector J4 changes from "1" to "0".
3. The motor 20 turns clockwise and advances the piston shifter 23 until it contacts the piston. The switch contact 35 mounted on the piston 28 is then connected to pin 1 of connector J10. When the piston shifter 23 contacts the switch contact 35, pins 1 and 2 of connector J10 are shorted, and as a result, contacts of a relay K2 are closed, and remain closed until the device power is down. When the relay K2 is closed, the signal I/O2 fed to pin 4 of connector J4 changes from "0" to "1".
4. The velocity is reprogrammed to lower velocity, for slow injection flow rate.
5. The output I/O1 of the motor 20 is programmed to "1" and is fed to the motor 8.
6. The motor 20 waits until the skin contact sensor 53 detects contact with the skin. As explained above, the skin contact sensor 53 is connected to J2 and the transistor Q1 connected to pin 2 of connector J2 starts conducting only when the sensor 53 makes contact with the surface of the skin. As a result signal IN2 at pin 5 of connector J4 changes from "0" to "1".
7. The motor 20 turns clockwise a predetermined number of microsteps, depending on the volume of material to be injected.
8. The motor 20 waits 20 seconds.
9. The output I/O1 of the motor 20 is programmed to "0" and is fed to the motor 8.
10. Go to step 5.

Explanation of Additional Hardware:
1. There is external power supply that is able to supply 24V 5A. Since we are using 15 Vdc and 5 Vdc in our electronic circuit, we used a voltage regulator L7815 (U1) to create a 15V voltage and used a voltage regulator L7805 (U3) to create a 5V voltage.
2. In order to prevent injury to the person being treated, two sensors are provided as follows. The limit switch contact 16 connected to the connector J7 is placed at the fully extracted "end of travel" position of the injector sub-assembly 300. Likewise, the switch contact 33 connected to the connector J5 is placed at the extended "end of travel" position of the piston. The 24V power is supplied to the electronic circuit and to the motors 8 and 20 through the normally closed relay K1. The relay's coil is permanently connected to the 12V, but is not connected to the ground. Only in case that one or both of the above-mentioned contacts 16 or 33 is shorted, whereby pin 1 of J5 is shorted to pin 2; and/or pin 1 of J7 is shorted to pin 2, then the relay's coil is connected to GND and the 24V supply to the electronic circuit and to the motors 8 and 20 is stopped instantly, without any delay. This prevents any possible disruption of the injection process, and any possible patient injury.

In an embodiment of the invention reduced to practice, the motors that were used are SilverPak 17C/CE made by LIN Engineering of Morgan Hill, Calif. 95037, USA. This motor is combination of a step motor, controller and driver. It can communicate with a personal computer (PC) via a RS485 interface, thus allowing the motor controller to be programmed via a USB to RS485 converter card.

It will be appreciated that while a specific embodiment has been described, the description is non-limiting and many changes may be made without departing from the scope of the invention, which is limited only by the attached claims. For example, although semi-automatic operation has been described whereby the injector sub-assembly and the displacement sub-assembly are advanced by stepper motors under control of a programmable controller, completely manual operation may be used without the need for either the stepper motors or the programmable controller.

Likewise, while screw rods in association with nuts are used to convert rotary motion of the stepper motors to linear movement of the injector sub-assembly, it will be apparent that the same effect can be realized using a worm gear and linear toothed guide. The displacement sub-assembly as described is manually operated but can be automated.

It will also be appreciated that while in the embodiment as described, a syringe is used to inject the material, the device may include other forms of receptacle for containing the material and the material may be released using other means. By way of example, a fixed flexible container may be provided and material may be released by applying pressure to the container as is done is tubes of toothpaste and the like or by applying gas pressure. The needle may be fixed directly to a container within the casing as in the case of a syringe or it can be fixed to the casing and material can be fed to the needle from a remote source that does not necessarily have to part of the device but is coupled thereto, for example by means of a flexible tubing.

In order to inject material the needle must penetrate the skin to a predetermined depth of penetration, which may be preset by the manufacturer or by the user, for example by fixing to the needle a mechanical stop that may be adjustable. Alternatively, if may be controlled as disclosed in the above description using a motor. In either case, an indication of the location of the tip of the needle relative to the user's skin may be obtained via feedback from a skin sensor mounted in known spatial disposition with the needle. This may be used to alert the user that the tip of the needle is ready for injecting material promoting him or her to press a manual lever to move the needle a preset distance so as to penetrate the skin. Alternatively, it may be used to alert the user that the needle has penetrated by a preset distance so as to prompt the user to remove the needle and move it along the treatment path for the next injection. In the case of automatic devices the feedback may be used by a controller to effect penetration to the required depth.

Likewise, while in the embodiment as described, electrically operated stepper motors are used to move the injection sub-assembly it will readily be appreciated that other forms of power may be employed, such as manual, pneumatic and hydraulic devices. Manually operated mechanisms may be spring biased so as to adjust the tension in a spring according to a required degree of advancement or penetration of the needle, such that releasing the spring under control of a manual lever or dial or the like, moves the needle by a pre-calibrated distance.

The invention claimed is:

1. A device for successively injecting material into a skin surface, said device comprising:
an injector sub-assembly having a needle configured for injecting said material into body tissue, and
a displacement sub-assembly configured to operate automatically only when the injector sub-assembly is retracted and to allow precise displacement of the needle or of the device along a path that lies in a plane of the skin surface between successive injections whereby the device is moved automatically or manually a predetermined, controlled distance laterally across the skin surface between each successive injection.

2. The device according to claim 1, wherein the injector sub-assembly is configured to control a speed at which the needle is inserted into the body tissue.

3. The device according to claim 1, wherein the device is adapted to inject said material at a predetermined depth of penetration to body tissue.

4. The device according to claim 1, wherein the device is adapted to inject a predetermined amount of said material into the body tissue in each injection.

5. The device according to claim 1, wherein the device is adapted to inject said material into the body tissue at a controlled flow-rate.

6. The device according to claim 1, including a track for slidably supporting the injector sub-assembly or the needle.

7. The device according to claim 1, including an integral removable disposable container for storing said material.

8. The device according to claim 1, wherein the injector sub-assembly is adapted for manual operation.

9. The device according to claim 1, wherein the displacement sub-assembly is adapted for manual operation.

10. The device according to claim 1, further including a controller responsively coupled to a camera or an optical device or a sensor mounted in association with the device for controlling at least one of the needle or the device displacement.

11. The device according to claim 1, further including a camera or an optical device or a sensor mounted in association with the device for providing feedback to a user to allow the user to control at least one of the needle or the device displacement.

12. The device according to claim 1, wherein the needle or device displacement is controlled by a user according to an optical or mechanical pointer placed on the device.

13. The device according to claim 1, including or being adapted for coupling to a source of energy for operating the injector sub-assembly.

14. The device according to claim 1, including or being adapted for coupling to a source of energy for operating the displacement sub-assembly.

15. The device according to claim 13, including a controller for controlling operation of the injector sub-assembly.

16. The device according to claim 14, including a controller for controlling operation of the displacement sub-assembly.

17. The device according to claim 1, wherein the injector sub-assembly comprises:
a carriage supporting said needle, said carriage being slidably supported by a fixed support within the device, and
a first drive unit coupled to the carriage for inducing displacement thereof.

18. The device according to claim 17, further including:
a controller coupled to the first drive unit for advancing the carriage a predetermined distance.

19. The device according to claim 1, wherein the injector sub-assembly comprises:
a carriage supporting said needle, said needle being slidably supported on said carriage, and
a second drive unit operable for releasing a desired quantity of material through the needle.

20. The device according to claim 19, further including:
a controller coupled to the second drive unit for releasing a controlled quantity of material.

21. The device according to according to claim 1, wherein an injection depth limiter is mountable in association with the needle.

22. The device according to according to claim 1, wherein:
an injection depth limiter is mountable in association with the needle and is operable to obtain a skin contact signal for providing an indication regarding a position of the needle relative to a person's skin surface.

23. The device according to according to claim 22, wherein the injection depth limiter comprises two mutually insulated contacts supported by a plastic electrically insulating tube of complementary shape to a base of the needle, and being adapted for mounting on a base of the needle such that the contacts are always at the same distance from an end of the needle.

24. The device according to according to claim 22, wherein a bore is formed in an end of the plastic tube intermediate the two contacts for avoiding permanent conductance associated with residual fluid, that might otherwise short the contacts thereby jeopardizing the correct operation of the injection depth limiter.

25. The device according to according to claim 1, wherein the needle is at least partially surrounded by safety stop that prevents inadvertent penetration of the needle prior to injection.

26. The device according to claim 10, wherein:
a first pair of switch contacts is mounted in fixed spatial relationship to the injector sub-assembly each for effecting electrical contact with the injector sub-assembly at a respective opposite end of a permitted travel thereof.

27. The device according to claim 26, including a controller coupled to the first pair of switch contacts and to a moving contact mounted on the injector sub-assembly and being responsive to contact between the moving contact and either of the first pair of switch contacts for disabling fluther advancement in either direction of the injector sub-assembly.

28. The device according to claim 26, wherein:
a second pair of switch contacts is mounted in fixed spatial relationship to the injector sub-assembly each for effecting electrical contact with a release unit operated by the second drive unit at a respective opposite end of a permitted travel thereof.

29. The device according to claim 28, including a controller coupled to the second pair of switch contacts and to a moving contact mounted on the release unit and being responsive to contact between the moving contact and either of the second pair of switch contacts for disabling further advancement in either direction of the release unit.

30. The device according to claim 7, wherein:
the release unit is a piston shifter that is operable to release material from the container, and
a forward contact of said second pair of switch contacts is located in such a position that the piston shifter will reach and make contact with the forward contact a short distance before the piston reaches an end of the container.

31. The device according to claim 1, wherein the displacement sub-assembly comprises:
a feeler arm articulated to the injector sub-assembly so as to be brought into contact with the skin when the injection needle is withdrawn;
a controller being responsive to said contact for alerting a user that the injection needle is withdrawn and prompting him or her to manually move the device along the treatment path for a subsequent injection.

32. The device according to claim 31, wherein:
movement of the device along the treatment path while the feeler arm is in contact with the skin induces rotation of the displacement sub-assembly thereby laterally displacing the device along the treatment path, and
a sensor is operatively coupled to the device for sensing a specified degree of rotation of the displacement sub-assembly and for prompting the user to cease further movement of the device.

33. The device according to claim 1, wherein the displacement sub-assembly is coupled to the injector sub-assembly so as to be operative only when the needle is retracted and being configured to facilitate precise displacement of the device along said path between successive injections.

* * * * *